United States Patent [19]

Papadopoulou-Rosenzweig et al.

[11] Patent Number: 5,294,715
[45] Date of Patent: Mar. 15, 1994

[54] ACRIDINE-INTERCALATOR BASED HYPOXIA SELECTIVE CYTOTOXINS

[75] Inventors: Maria Papadopoulou-Rosenzweig; William D. Bloomer, both of Pittsburgh, Pa.; William D. Bloomer, both of Pittsburgh, Pa.

[73] Assignee: University of Pittsburgh, Pittsburgh, Pa.

[21] Appl. No.: 649,703

[22] Filed: Feb. 1, 1991

[51] Int. Cl.[5] .......................................... C07D 233/91
[52] U.S. Cl. .................................... 546/106; 514/297
[58] Field of Search .......................................... 546/106

[56] References Cited

U.S. PATENT DOCUMENTS

| | | | |
|---|---|---|---|
| 4,954,515 | 9/1990 | Suto | 548/229 |
| 5,073,639 | 12/1991 | Suto | 548/229 |

OTHER PUBLICATIONS

Denny et al. Chem. Abstr. vol. 116 Entry 190298n (1992).
Panicucci et al. Int. J. Radiation Oncology Biol. Phys. vol. 16 pp. 1039-1043 (1989).
Roberts, Int. J. Radiation, Biol. vol. 51 641-54 (1987).
Roberts, Radiation Res. vol. 123 pp. 153-164 (1990).
Denny et al. Int. J. Radiation Oncology Biol. Phys vol. 22 pp. 553-556.
Alper, T., et al Nature 178:978-979 (1956).
Dische, S., et al Br. J. Radiol., 56:251-255 (1983).
Churchill-Davidson, I., et al, Lancet 1:1091-1095 (1955).
Bush, R. S., et al., Br. J. Cancer 37 (Suppl. III):302-306 (1978).
McNally, N. J., *Int. J. Radiat. Oncol. Biol. Phys.* 8:593-598 (1982).
Overgaard J., et al., Progress in Radio-Oncology III, Proceedings of the 3rd International Meeting on Progress in Radio-Oncology, Mar. 1985, 137-147, J.C.R.O., Vienna, (1987).
Coleman, C. N., et al., Int. J. Radiat. Oncol. Biol. Phys. 10:1749-1753 (1984).
Roberts, J. T., et al., Int. J. Radiat. Oncol. Biol. Phys. 10:1755-1758 (1984).
Saunders, M. I. et al., Int. J. Radiat. Oncol. Biol. Phys. 10:1759-1763 (1984).
Adams, G. E., et al., Br. J. Cancer 49:571-577 (1984).
Stratford, I. J., et al, Int. J. Radiat. Biol. 55:411-422 (1989).
Nias, A. H. W., Int. J. Radiat Biol. 48:297-314 (1985).
Ahmed, I., et al., Int. J. Radiat. Oncol. Biol. Phys. 12:1079-1081 (1986).
Sieman, D. W., Int. J. Radiat. Oncol. Biol. Phys. 10:1585-1594 (1984).
Brown, J., Int. J. Radiat. Oncol. Biol. Phys. 16:987-993 (1984).
Stratford, M. R. L., et al., Int. J. Radiat, Oncol. Biol. Phys. 16:1007-1010 (1989).
Chibber, R., et al. Int. J. Radiat. Oncol. Biol. Phys. 10:1213-1215 (1984).
Teicher, B. A., et al., Int. J. Radiat Oncol. Biol. Phys. 11:937-941 (1985).
Skov, K. et al., Int. J. Radiat. Biol. 52:289-297 (1987).
Chan, P. K. L., et al. Int. J. Radiat. Oncol. Biol. Phys. 12:1059-1062 (1986).

(List continued on next page.)

*Primary Examiner*—Donald G. Daus

[57] ABSTRACT

Hypoxia selective cytotoxins of the general formula

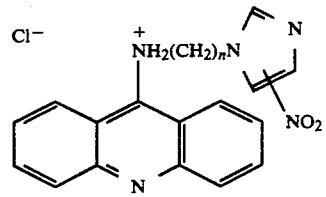

wherein n is from 1 to 5, and $NO_2$ is in at least one of the 2, 4 or 5-positions of the imidazole. Such compounds have utility as radiosensitizers and chemosensitizers.

4 Claims, 7 Drawing Sheets

OTHER PUBLICATIONS

Chan, P. K. L., et al., Int. J. Radiat. Biol., 52:49–55 (1987).

Butler, J., et al., Radiation Research 102:1–13 (1985).

Panicucci, R., et al., Int. J. Radiat. Oncol. Biol. Phys. 16:1039–1043 (1989).

Wilson, W. R., et al., Br. J. Cancer 49:215–223 (1984).

Roberts, P. B., et al., Int. J. Radiat. Biol. 51:641–654 (1987).

Roberts, P. B., et al., Radiation Research 123–153–164 (1990).

Wilson, W. R., et al., Int. J. Radiat. Oncol. Biol. Phys. 12:1235–1238 (1983).

Adams, G. E., et al., Chemical Abstracts 102:6489n (1985).

Stratford, I. J., et al., Int. J. Radiat. Oncol. Biol. Phys. 16:973–976 (1989).

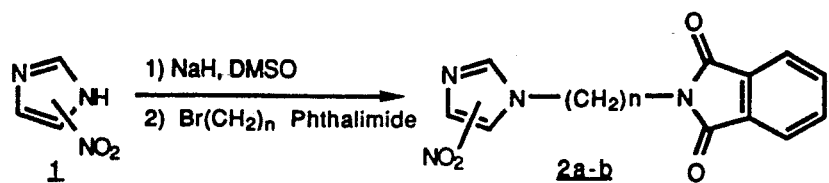
FIGURE 1a
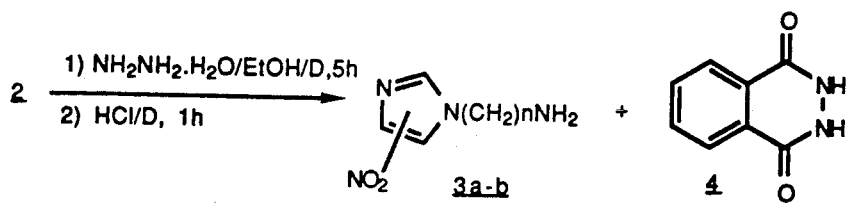
FIGURE 1b
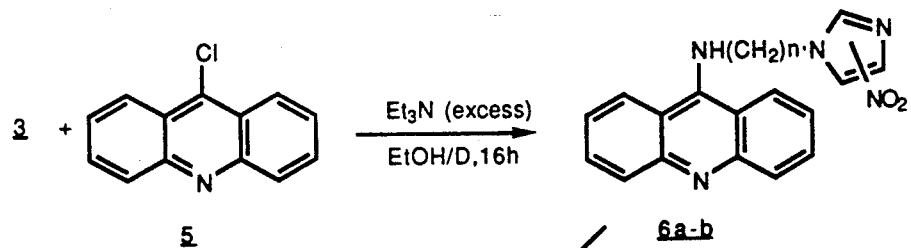
FIGURE 1c
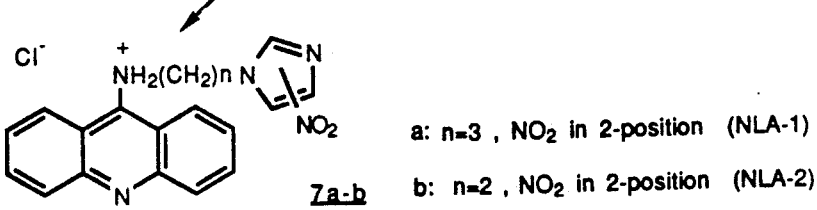
a: n=3, $NO_2$ in 2-position (NLA-1)
b: n=2, $NO_2$ in 2-position (NLA-2)

ACRIDINE-INTERCALATOR BASED HYPOXIA SELECTIVE CYTOTOXINS

ACKNOWLEDGMENT

The present invention was developed in part with Government support under Subcontract No. DE-FG02-89ER60869 awarded by the Department of Energy. The Government has certain rights in this invention.

FIELD OF THE INVENTION

The present invention relates generally to cancer therapy, and more particularly is directed to compounds and methods for enhancing radiation and chemotherapy responses of tumor cells.

BACKGROUND OF THE INVENTION

The use of radiation and/or chemotherapy in clinical cancer treatments is often unsuccessful for a number of reasons. For example, there is considerable evidence that oxygen deficient tumor cells, known as hypoxic cells, may be resistant to radiotherapy. See, Alper, T., et al., *Nature* 178:978-979 (1956); Dische, S., et al., *Br. J. Radiol.*, 56:251-255 (1983); Churchill-Davidson, I., et al., *Lancet* 1:1091-1095 (1955); and Bush, R. S., et al., *Br. J. Cancer* 37 (*Suppl. III*):302-306 (1978), the disclosures of which are incorporated herein by reference. Hypoxic tumor cells may also be preferentially spared by some commonly used anti-cancer agents because of their location in poorly vascularized areas of tumors or their cell cycle state as reported by McNally, N. J., *Int. J. Radiat. Oncol. Biol. Phys.* 8:593-598 (1982), the disclosure of which is incorporated herein by reference.

Efforts to overcome hypoxia in clinical treatments of cancer have led to the development of hypoxic cell radiosensitizers which substitute for oxygen in radiochemical reactions. In particular, clinical trials with the hypoxic cell radiosensitizer misonidazole (MISO), an electron-affinic 2-nitroimidazole, have shown some benefit in certain situations, as reported by Overgaard, J., et al., *Progress in Radio-Oncology III, Proceedings of the 3rd International Meeting on Progress in Radio-Oncology*, March 1985, 137-147, J.C.R.O., Vienna, 1987, the disclosure of which is incorporated herein by reference. However, MISO has shown significant neurotoxicity such that the total dose of the drug administered to a patient is limited.

Radiation sensitizers of this type are hypoxia selective, meaning that such compounds are considerably more toxic to hypoxic cells relative to aerobic cells. This differential hypoxic cytotoxicity is due to bioreductive activation of the drug under anaerobic conditions. For this reason hypoxia selective cytotoxins are also referred to as bioreductive agents. Bioreductive agents are therefore potentially exploitable in cancer therapy.

At the present time, at least three other 2-nitroimidazole derivatives are undergoing clinical evaluation as hypoxic cell radiosensitizers. Etanidazole (SR-2508), a neutral agent which is more hydrophilic than MISO, is less neurotoxic in experimental animals and can be administered to humans at about a threefold higher dose than MISO as reported by Coleman, C. N., et al., *Int. J. Radiat. Oncol. Biol. Phys.* 10:1749-1753 (1984), the disclosure of which is incorporated herein by reference. Roberts, J. T., et al., *Int. J. Radiat. Oncol. Biol. Phys.* 10:1755-1758 (1984) and Saunders, M. I., et al., *Int. J. Radiat. Oncol. Biol. Phys.* 10:1759-1763 (1984), the disclosures of which are incorporated herein by reference, report that pimonidazole (Ro 03-8799) contains a basic piperidine moiety and has a total dose limitation similar to that of MISO. RSU-1069 is a bifunctional molecule containing a 2-nitroimidazole group and an alkylating aziridine. In experimental systems the RSU-1069 bioreduction agent has substantially greater activity than MISO as reported by Adams, G. E., et al., *Br. J. Cancer* 49:571-577 (1984); Stratford, I. J., et al., *Int. J. Radiat. Biol.* 55:411-422 (1989); Nias, A. H. W., *Int. J. Radiat. Biol.* 48:297-314 (1985); and Ahmed, I., et al., *Int. J. Radiat. Oncol. Biol. Phys.* 12:1079-1081 (1986), the disclosures of which are incorporated herein by reference. For example, Adams, G. E., et al., *Br. J. Cancer* 49:571-577 (1984) reports that bioreductive agent RSU-1069 is toxic to hypoxic cells in vitro at about a 100-fold lower concentration when compared to the toxic concentration for aerobic cells. The high differential cytotoxic activity of RSU-1069 is believed to be due to the formation of a very reactive, bifunctional electrophile upon the compound being reduced in cells.

Bioreductive radiosensitizers have also been shown to significantly enhance the activity of several chemotherapeutic agents, such as, for example, cyclophosphamide, nitrosoureas, and L-phenylalanine mustard in vitro and in vivo as reported by McNally, N. J., *Int. J. Radiat. Oncol. Biol. Phys.* 8:593-598 (1982); and Sieman, D. W., *Int. J. Radiat. Oncol. Biol. Phys.* 10:1585-1594 (1984), the disclosures of which are incorporated herein by reference. This enhancement of chemotherapeutic activity is known as chemosensitization or chemopotentiation.

Currently there is increasing interest in targeting bioreductive agents to DNA in order to improve the cytotoxicity of such agents. See Brown, J., *Int. J. Radiat. Oncol. Biol. Phys.* 16:987-993 (1984); and Nias, A. H. W., *Int. J. Radiat. Biol.* 48:297-314 (1985), the disclosures of which are incorporated herein by reference. As reported by Stratford, M. R. L., et al., *Int. J. Radiat. Oncol. Biol. Phys.* 16:1007-1010 (1989), the disclosure of which is incorporated herein by reference, it is the concentration of sensitizer within DNA as opposed to the average intracellular concentration which appears to be the major factor that determines cytotoxic efficacy. One such DNA targeting effort involves combining an alkylating agent with bioreductive functional groups within the same drug. See, for example, Adams, G. E., et al., *Br. J. Cancer* 49:571-577 (1984). Other efforts of groups such as Chibber, R., et al. *Int. J. Radiat. Oncol. Biol. Phys.* 10:1213-1215 (1984); Teicher, B. A., et al., *Int. J. Radiat. Oncol. Biol. Phys.* 11:937-941 (1985); Skov, K. et al., *Int. J. Radiat. Biol.* 52:289-297 (1987); Chan, P. K. L., et al. *Int. J. Radiat. Oncol. Biol. Phys.* 12:1059-1062 (1986); and Chan, P. K. L., et al., *Int. J. Radiat. Biol.* 52:49-55 (1987), the disclosures of which are incorporated herein by reference, employed transition metal coordination complexes such as platinum and ruthenium to target nitroaromatic radiosensitizers to DNA. However, as reported by Butler, J., et al., *Radiation Research* 102:1-13 (1985), the disclosure of which is incorporated herein by reference, these metal coordination complexes are often less effective as radiosensitizers than the free radiosensitizer molecule, despite the fact that the one electron reduction potential (a chemical property related to sensitization efficiency) can be increased in some platinum complexes compared to the free sensitizer ligand.

Another approach for targeting bioreductive agents to DNA involves use of an intercalating moiety such as phenanthridine or acridine which is inserted between the base pairs of the DNA. For example, NLP-1, 5-[3-(2-nitro-1-imidazoyl)-propyl]-phenanthridinium bromide, a 2-nitroimidazole-linked phenanthridine, has been synthesized and its hypoxic cell cytotoxicity and radiosensitization has been estimated by Panicucci, R., et al., *Int. J. Radiat. Oncol. Biol. Phys.* 16:1039–1043 (1989), the disclosure of which is incorporated herein by reference. Nitracrine, 1-nitro-acridine, is a potent hypoxia selective cytotoxin and a radiation sensitizer in mammalian cell culture, however, its rapid metabolism limits its radiosensitization efficacy in vivo. See, Wilson, W. R., et al., *Br. J. Cancer* 49:215–223 (1984); Roberts, P. B., et al., *Int. J. Radiat. Biol.* 51:641–654 (1987); Roberts, P. B., et al., *Radiation Research* 123:153–164 (1990); and Wilson, W. R., et al., *Int. J. Radiat. Oncol. Biol. Phys.* 12:1235–1238 (1983), the disclosures of which are incorporated herein by reference.

An acridine conjugated hypoxia selective cytotoxin that is relatively stable in vivo is desirable since acridine is a better intercalator than phenanthridine, as reported by Roberts, P. B., et al., *Int. J. Radiat. Biol.* 51:641–654 (1987). Non-covalent binding to DNA, such as by intercalation, may allow migration of the radiosensitizer to DNA sites where radiation induced radicals are created. Thus, as reported by Roberts, P. B., et al., *Radiation Research* 123:153–164 (1990) 1-nitracrine which exhibits faster dissociation kinetics of its DNA-drug complex than the other nitroacridine isomers is a 20-fold more potent sensitizer than other isomers tested.

Accordingly, there is a need for bioreductive activated cytotoxins which enhance the cytotoxic activities of ionizing radiation and chemotherapeutic agents to hypoxic cells without substantial aerobic toxicity.

SUMMARY OF THE INVENTION

Accordingly, it is a primary object of the present invention to provide hypoxia selective cytotoxins which do not exhibit significant aerobic toxicity.

Another object of the present invention is to provide hypoxia selective cytotoxins which bind to DNA through intercalation and/or a protonated amino functionality.

Yet another object of the present invention is to provide hypoxia selective cytotoxins which also exhibit radiosensitization properties.

Still another object of the present invention is to provide hypoxia selective cytotoxins which also exhibit chemosensitization properties.

Still another object of the present invention is to provide methods of treating cancer using the novel hypoxia selective cytotoxins of the present invention.

These and other objects of the present invention are achieved by one or more of the following embodiments.

In one aspect, the invention features hypoxia selective cytotoxins of the general formula

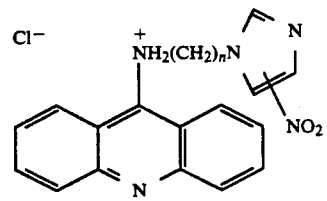

wherein n is from 1 to 5, and is preferably 2 or 3, and $NO_2$ is in at least one of the 2,4, or 5-positions of the imidazole, preferably in the 2-position. Specifically, the present invention is directed to the compounds 9-[3-(2-nitro-1-imidazolyl) propylamino] acridine hydrochloride (NLA-1) and 9-[2-(2-nitro-1-imidazolyl) ethylamino] acridine hydrochloride (NLA-2).

In a preferred embodiment the invention features 9-[3-(2-nitro-1-imidazolyl) propylamino] acridine hydrochloride (NLA-1).

In another preferred embodiment the invention features 9-[2-(2-nitro-1-imidazolyl) ethylamino] acridine hydrochloride (NLA-2).

In another aspect, the invention features a method of radiosensitization, comprising treatment with ionizing radiation and an effective amount of an hypoxia selective cytotoxin of the general formula

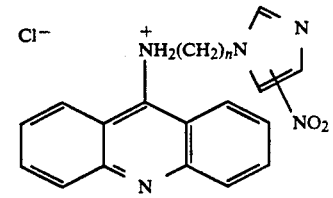

wherein n is from 1 to 5, and $NO_2$ is in at least one of the 2, 4 or 5-positions of the imidazole.

In yet another aspect, the invention features a method of chemosensitization, comprising treatment with a chemotherapeutic agent and an affective amount of an hypoxia selective cytotoxin of the general formula

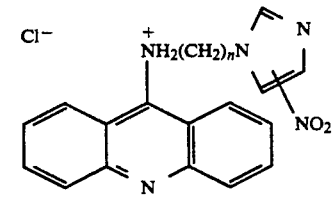

wherein n is from 1 to 5, and $NO_2$ is in at least one of the 2, 4 or 5-positions of the imidazole.

In still another aspect, the invention features a method of targeting a hypoxia selective cytotoxin to the DNA of hypoxic tumor cells, comprising treatment with compounds of the general formula

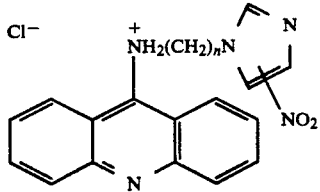

wherein n is from 1 or 5, and NO₂ is in at least one of the 2, 4 or 5-positions of the imidazole.

The present compounds are particularly well suited as hypoxia selective cytotoxins due to their common features of a 2-nitroimidazole moiety as the hypoxia-selective sensitizing moiety which is linked to an acridine ring at the 9-position through an alkylamino chain (propyl-amino chain for NLA-1 or an ethyl-amino chain for NLA-2) for targeting the sensitizing moiety to DNA through intercalation. The compounds also feature an amino functionality in its protonated form to increase the sensitizer concentration near the negatively charged phosphates of the DNA backbone.

Other features and advantages of the invention will be apparent from the following description of the preferred embodiment, and from the claims.

DESCRIPTION OF THE DRAWINGS

FIG. 1 shows schematic reaction pathways for synthesizing the novel hypoxia selective cytotoxins of the present invention.

DETAILED DESCRIPTION OF THE INVENTION

Figure 2A:
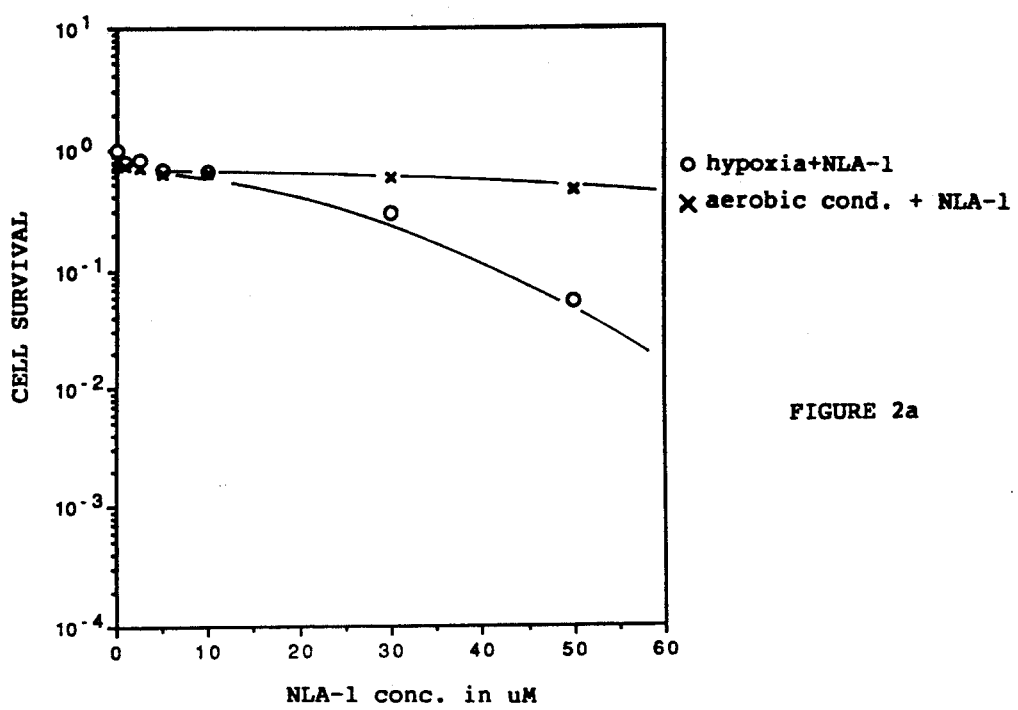
FIGS. 2a and 2b are graphs showing respectively, cytotoxicity of NLA-1 as a function of its concentration in V-79 Chinese hamster cells after 1 hour of exposure under hypoxic (◯) and aerobic (×) conditions; and cytotoxicity of NLA-2 as a function of its concentration in V-79 Chinese hamster cells after 1 hour of exposure under hypoxic (◯) and aerobic (×) conditions.

The preparation of the novel compounds of the present invention is illustrated diagramatically in FIG. 1 and is illustrated in Examples 1 and 2 below for NLA-1 and NLA-2, respectively. In all cases melting points of compounds were determined on a Mel-Temp II (Mel-Temp Laboratory Devices, Holiston, Mass.) open capillary melting point apparatus. ¹H NMR spectra were determined on a Brucker 300 (300 MHz) spectrometer. Low resolution mass spectra (MS) were obtained on a VG 7070 double focusing mass spectrometer, at 70 eV ion source at 210° C. High resolution mass spectra (HRMS) were obtained on a Varian CH-5 double focusing reverse geometry mass spectrometer by peak matching technique, at 70 eV ion source at 210° C. All commercial reagents were obtained from Aldrich Co. or Eastman Kodak Co. and were utilized without further purification.

EXAMPLES

EXAMPLE 1

Nitroimidazolylakyl phthalimides represented as intermediate compound 2a in FIG. 1 were generally prepared by first dissolving 120 mg of nitroimidazole in 5 ml dry dimethysulfoxide (DMSO) and then carefully adding with stirring 42.47 mg NaH (60% dispersion in mineral oil) under argon atmosphere and exclusion of water. After the reaction mixture became clear, 290.4 mg (98% purity) of 3-bromopropylphthalimide was added in one portion and the mixture was stirred at room temperature for 48 hours. After the bromoalkylphthalimide disappeared as ascertained by thin layer chromotography (TLC), thereby indicating the end of the reaction, DMSO was removed by distillation under low pressure and the remaining residue was triturated with CH₂Cl₂/H₂O. The resulting organic layer was dried with Na₂SO₄, and then filtered, and evaporated. The products were usually white solids which were identified by ¹H NMR and high resolution mass spectrometry (HRMS).

Compound 2a shown in FIG. 1, 3-(2-nitro-1-imidazolyl)propylphthalimide, is a white solid and was obtained at a yield of 82%. The following data were measured: m.p. 151°–153° C.; ¹H NMR (CDCl₃) δ:2.27 (q,J = 6.5 Hz, 2H); 3.78 (t,J = 6 Hz, 2H); 4.64 (t,J = 7 Hz, 2H); 7.16 (s, 1H); 7.36 (s, 1H); 7.73–7.90 (m, 4H); HRMS m/z 300.0842 calculated for $C_{14}H_{12}N_4O_4$; Found: 300.0841.

The compound 3a nitroimidazolylalkyl amine of FIG. 1 was prepared via a modified hydrazinolysis method as described by Adams, G. E., et al., UK Pat. Appl. 2,131,020 (1984), Chemical Abstracts 102:6489n (1985), the disclosure of which is incorporated herein by reference. 150 mg of the 2a phthalimide as shown in FIG. 1 and 25 mg (98% purity) of hydrazine monohydrate were refluxed in 2 ml of ethanol for 4.5–5 hours. The reaction mixture was then cooled and acidified with excess 1N HCl solution, and the acidified solution was again refluxed for 1 hour and cooled. The resulting insoluble phthalylhydrazide, compound 4 of FIG. 1, was filtered off, and the ethanol was removed by evaporation under low pressure. The solution was filtered again to remove the remaining phthalylhydrazide, alkalized with NaOH, and extracted 10 times with CH₂Cl₂. The organic layer was dried with Na₂SO₄, filtered, and evaporated to yield the 3a nitroimidazolylalkyl amine.

The 3a compound, 3-(2-nitro-1-imidazolyl) propyl amine, is a yellow oil which becomes orange over time and was obtained at a yield of 70–71%. The following data were obtained: $^1$H NMR (CDCl$_3$) δ:1.35 (br, 2H); 1.95 (q,J=6.96 Hz, 2H); 2.74 (t,J=6.54 Hz, 2H); 4.53 (t,J=7 Hz, 2H); 7.11 (s, 1H); 7.15 (s, 1H); MS:m/z of 170 (M+).

Compounds 6a and 7a of FIG. 1 were prepared as follows. 260 mg of the 3a amine and 326.5 mg of 9-chloroacridine were refluxed with 1.064 ml of dry Et$_3$N under argon atmosphere and exclusion of water in 6 ml absolute EtOH (100 mg/ml) for 12 hours. Upon heating, the mixture became clear, and at the end of refluxing, a bright yellow solid was formed. The solid was filtered off, washed repeatedly with acetone, and identified by $^1$H NMR and HRMS as the 7a hydrochloride shown in FIG. 1.

The remaining solution was evaporated and chromatographed on a preparative TLC plate (alumina, 1000 μm, ethyl acetate), to give as third band, after acridine and acridone the free amine 6a. The free amine 6a, 6b is converted into its HCl-salt by dissolving the compound in acetone and precipitating carefully with concentrated HCl.

Compound 7a, 9-[3-(2-nitro-1-imidazolyl) propylamino] acridine hydrochloride ("NLA-1"), is a yellow powder with a decomposition point of 258° C. Yield was 70%. The following data were measured: $^1$H NMR (D$_2$O) δ:2.44 (q,J=6 Hz, 2H); 4.20 (t,J=6 Hz, 2H); 4.49 (t,J=6 Hz, 2H); 6.65 (s, 1H), 7.17 (s, 1H); 7.44 (t,J 7.6 Hz, 2H); 7.6 (d,J=8.58 Hz, 2H); 7.88 (t,J=7.68 Hz, 2H); 8.02 (d,J=8.7 Hz, 2H); FAB: (in m-nitrobenzoic acid) Calculated for C$_{19}$H$_{18}$N$_5$O$_2$: 348; Found: 348; HRMS: Calculated for C$_{19}$H$_{17}$N$_5$O$_2$ (free amine 6a) 347.1382; Found: 347.1382.

EXAMPLE 2

Nitroimidazolylalklyl phthalimides represented as intermediate compound 2b in FIG. 1 were generally prepared by first dissolving 300 mg of nitroimidazole in 12 ml dry dimethysulfoxide (DMSO) and then carefully adding with stirring 106.2 mg of NaH (60% dispersion in mineral oil) under argon atmosphere and exclusion of water. After the reaction mixture became clear, 717.3 mg (94% purity) of 2-bromoethylphthalimide was added in one portion and the mixture was stirred at room temperature for 5 days. After the bromoalkylphthalimide disappeared according to thin layer chromatography (TLC) thereby indicating the end of the reaction, DMSO was removed by distillation under low pressure and the remaining residue was triturated with CH$_2$Cl$_2$/H$_2$O. The resulting organic layer was dried with Na$_2$SO$_4$, and then filtered, and evaporated. The products were usually white solids which were identified by $^1$H NMR and high resolution mass spectrometry (HRMS).

Compound 2b of FIG. 1, 2-(2-nitro-1-imidazolyl)ethylphthalimide, is a white solid and was obtained at a yield of 40–45%. The following data were measured: m.p. 187°–189° C.; $^1$H NMR (DCDl$_3$) δ:4.21 (t, J=4.4 Hz, 2H); 4.73 (t, J=6 Hz, 2H); 6.88 (s, 1H); 7.04 (s, 1H); 7.71–7.89 (m, 4H); MS:m/z 286; HRMS: Calculated for C$_{13}$H$_{10}$N$_4$O$_4$—NO$_2$:240.0773; Found: 240.0773.

The compound 3b nitroimidazolylalkyl amine of FIG. 1 was prepared via a modified hydrazinolysis method as described by Adams, G. E., et al., UK Pat. Appl. 2,131,020 (1984), *Chemical Abstracts* 102:6489n (1985). 230 mg of the 2b phthalimide as shown in FIG. 1 and 41.32 mg of hydrazine monohydrate were refluxed in 2.5 ml of ethanol for 4.5–5 hours. The reaction mixture was then cooled and acidified with excess 1N HCl solution, and the acidified solution was again refluxed for 1 hour and cooled. The resulting insoluble phthalylhydrazide, compound 4 of FIG. 1, was filtered off, and the ethanol was removed by evaporation under low pressure. The solution was filtered again to remove the remaining phthalylhydrazide, alkalized with NaOH, and extracted 10 times with CH$_2$Cl$_2$. The organic layer was dried with Na$_2$SO$_4$, filtered, and evaporated to yield the 3b nitroimidazolylalkyl amine.

Compound 3b, 2-(2-nitro-1-imidazolyl) ethyl amine, is a yellowish oil, with a yield of 45–50%. The following data were obtained: $^1$H NMR (DCDl$_3$) δ:1.51 (br, 2H); 2.75 (t, J=6Hz, 2H); 4.19 (t, J=6.5 Hz, 2H); 7.10 (S, 1H); 7.13 (s, 1H); MS:m/z of 156 (M+).

Compounds 6b and 7b of FIG. 1 were prepared as follows. 85 mg of the 3b amine and 118 mg of 9-chloroacridine were refluxed with 379 ml of dry Et$_3$N under argon atmosphere and exclusion of water in 2.5 ml absolute EtOH (100 mg/ml) for 12 hours. Upon heating, the mixture became clear, and at the end of refluxing, a bright yellow solid was formed. The solid was filtered off, washed repeatedly with acetone, and identified by $^1$H NMR and HRMS as the 7b hydrochloride shown in FIG. 1.

The remaining solution was evaporated and chromatographed on a preparative TLC plate (alumina, 1000 μm, ethyl acetate), to give as third band, after acridine and acridone the free amine 6b. The free amine 6b is converted into its HCl-salt by dissolving the compound in acetone and precipitating carefully with concentrated HCl.

Compound 7b, 9-[2-(2-nitro-1-imidazolyl) ethylamino] acridine hydrochloride ("NLA-2") is a yellow powder with a decomposition point of 255° C. and was obtained at a 60% yield. The following data were measured: $^1$H NMR (DMSO-6d) δ:4.61 (t,J=5.5 Hz, 2H), 4.94 (t,J=5.5 Hz, 2H); 7.09 (s, 1H), 7.55 (t,J=7.8 Hz, 2H); 7.64 (s, 1H); 7.90 (d,J=8.2 Hz, 2H); 8.00 (t,J=7 Hz, 2H); 8.48 (d,J=8.6 Hz, 2H); 9.73 (br t, 1H); FAB: (in thioglycerol) Calculated for C$_{18}$H$_{16}$N$_5$O$_2$; 334; Found: 334.

As indicated above, the compounds of the present invention are improved hypoxia selective cytotoxins that enhance the cytotoxic activities of radiation and certain chemotherapeutic agents on hypoxic cells. Concentration dependent cytotoxicity of novel compounds NLA-1 and NLA-2 under hypoxic or aerobic conditions were determined in the following example.

EXAMPLE 3

Chinese hamster V-79 cells were grown in RPMI 1640 medium (Mediatech) supplemented with 10% fetal calf serum. The cells were harvested and suspended in 25 ml Erlenmeyer flasks fitted with rubber caps at 5×10$^5$ cells (5 ml total volume). The flasks were maintained at 37° C. under aerobic conditions or made hypoxic by gassing with 97% N$_2$/3% CO$_2$ humidified gas mixture (Linde) for 1 hour, at which time a bioreductive agent, either NLA-1 or NLA-2, was added. The NLA-1 or NLA-2 were prepared as aqueous solutions diluted to the appropriate concentration with tissue culture medium. The cells were exposed to concentrations of NLA-1 or NLA-2 ranging from 0 μM to 50 μM for 1 hour under aerobic or hypoxic conditions. The cells were then plated for colony formation. The hypoxic cells were kept hypoxic until they were plated. The cytotoxicity results were determined by either an MTT colorimetic assay as described by Stratford, I. J., et al., *Int. J. Radiat. Oncol. Biol. Phys.* 16:973–976 (1989), the disclosure of which is incorporated herein by reference, or a colonogenic assay as described by Roberts, P. B., et al., *Radiation Research* 123:153–164 (1990), and are shown for NLA-1 and NLA-2 in FIGS. 2a and 2b respectively.

Figure 2B:
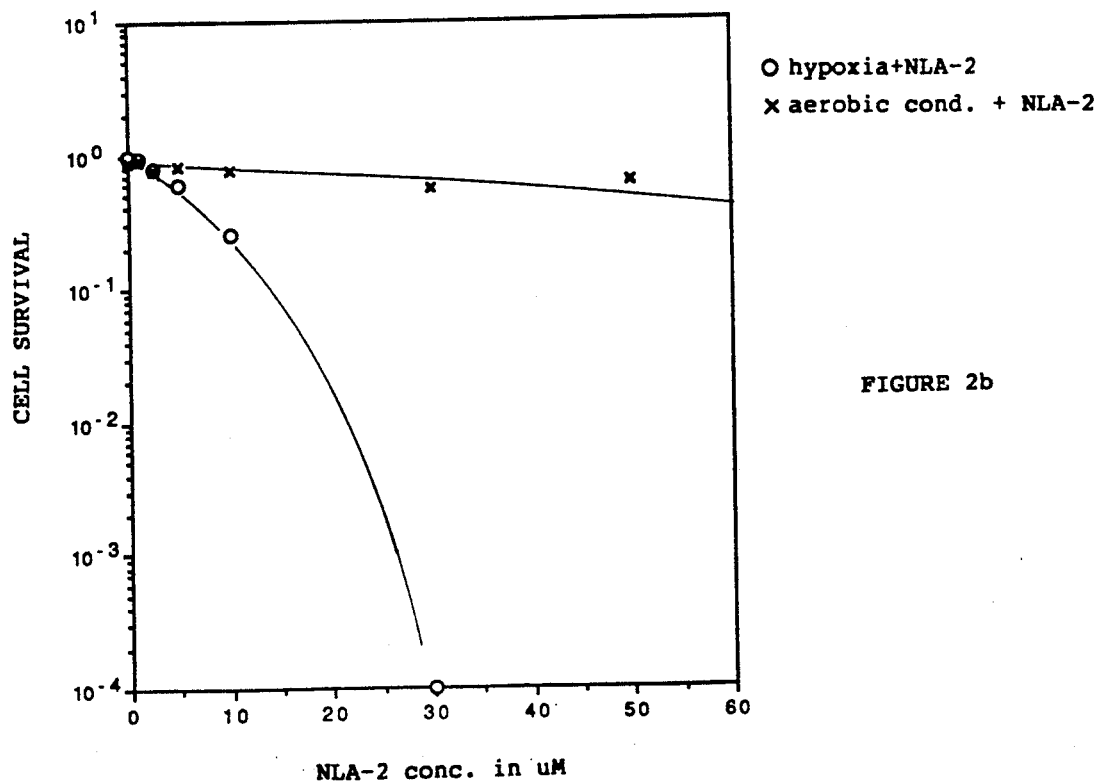

As seen in FIGS. 2a and 2b, NLA-1 and NLA-2 demonstrate dose dependent selective hypoxic cytotoxicity. No aerobic cytotoxicity was observed after incubation for 1 hour with 50 $\mu$M of either NLA-1 or NLA-2.

Time dependent toxicities of NLA-1 and NLA-2 under hypoxic or aerobic conditions were determined in the following example.

EXAMPLE 4

Figure 3A:
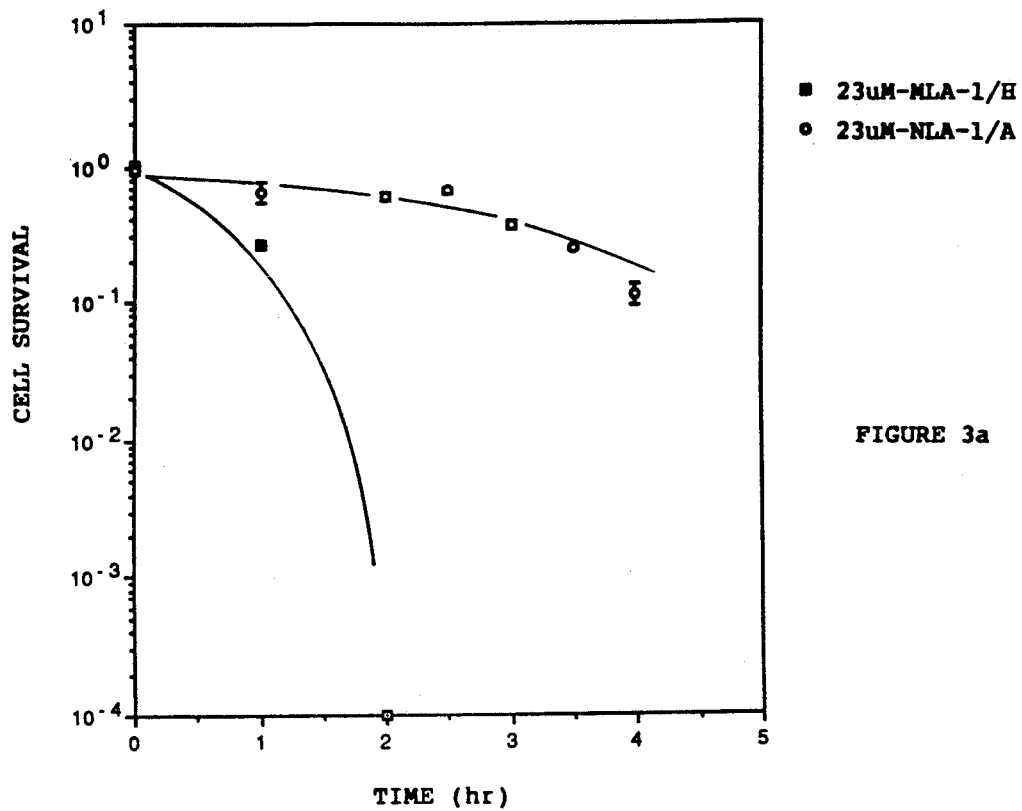
FIGS. 3a and 3b are graphs showing respectively, cytotoxicity of constant concentrations of NLA-1 (23 μM) as a function of time under hypoxic ( ▫ ) and aerobic (◯) conditions; and cytotoxicity of constant concentrations of NLA-2 (5 μM) as a function of time under hypoxic ( ▫ ) and aerobic (◯) conditions.
Figure 3B:
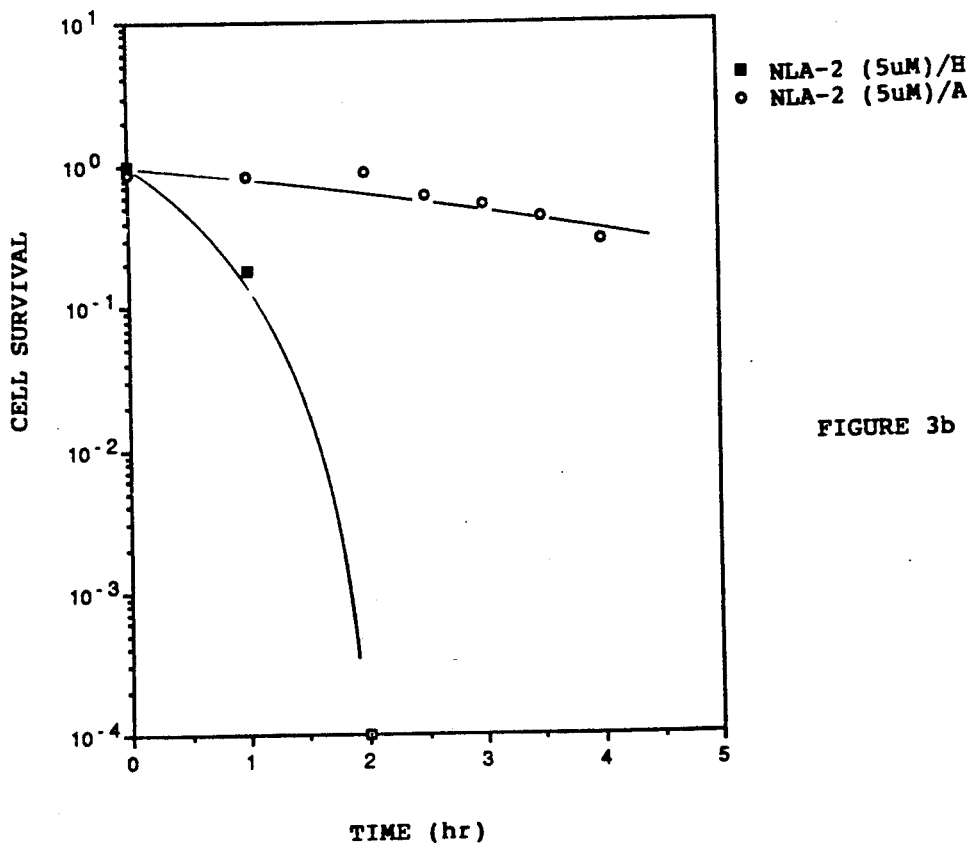

Chinese hamster V-79 cells were grown, harvested, and exposed to bioreductive agents as described in Example 3 except that the cells were exposed to one concentration of either NLA-1 or NLA-2 for various times ranging from 0–4 hours. NLA-1 was used at a concentration of 23 $\mu$M; NLA-2 was used at a concentration of 5 $\mu$M. The results are shown in FIGS. 3a and 3b, respectively. NLA-2 causes greater than 50% cell death within 1 hour at 5 $\mu$M, whereas NLA-1 treatment results in the same survival fraction within 1 hour at 23 $\mu$M. There was also a slight aerobic cytotoxicity after 4 hours of exposure to each compound.

In the following example the isosensitization points (ISP) of NLA-1 and NLA-2 were determined. ISP is defined as that drug concentration which is not toxic to aerobic cells and results in the same survival fraction upon exposure of hypoxic or oxygenated cells to a specified radiation dose.

EXAMPLE 5

Chinese hamster V-79 cells were cultured as in Example 2. NLA-1, NLA-2, NLP-1 (5-[3-(2-nitro-1-imidazolyl)propyl]phenanthridinium bromide), NEA (2-[2-nitro-1-imidazolyl]ethylamine) and MISO were added to aerated or hypoxic cells at concentrations ranging from 0 to $10^3$ $\mu$M. After 1 hour exposure to the various compounds, the cells were irradiated at 750 rads using a $^{137}$Cs irradiator (400 rads/min., room temp.). The irradiated cells were then plated in 4 well tissue culture plates (Flow Laboratories) for four days. Cell survival was determined by either the MTT or clonogenic assay as described in Example 3.

Figure 4:
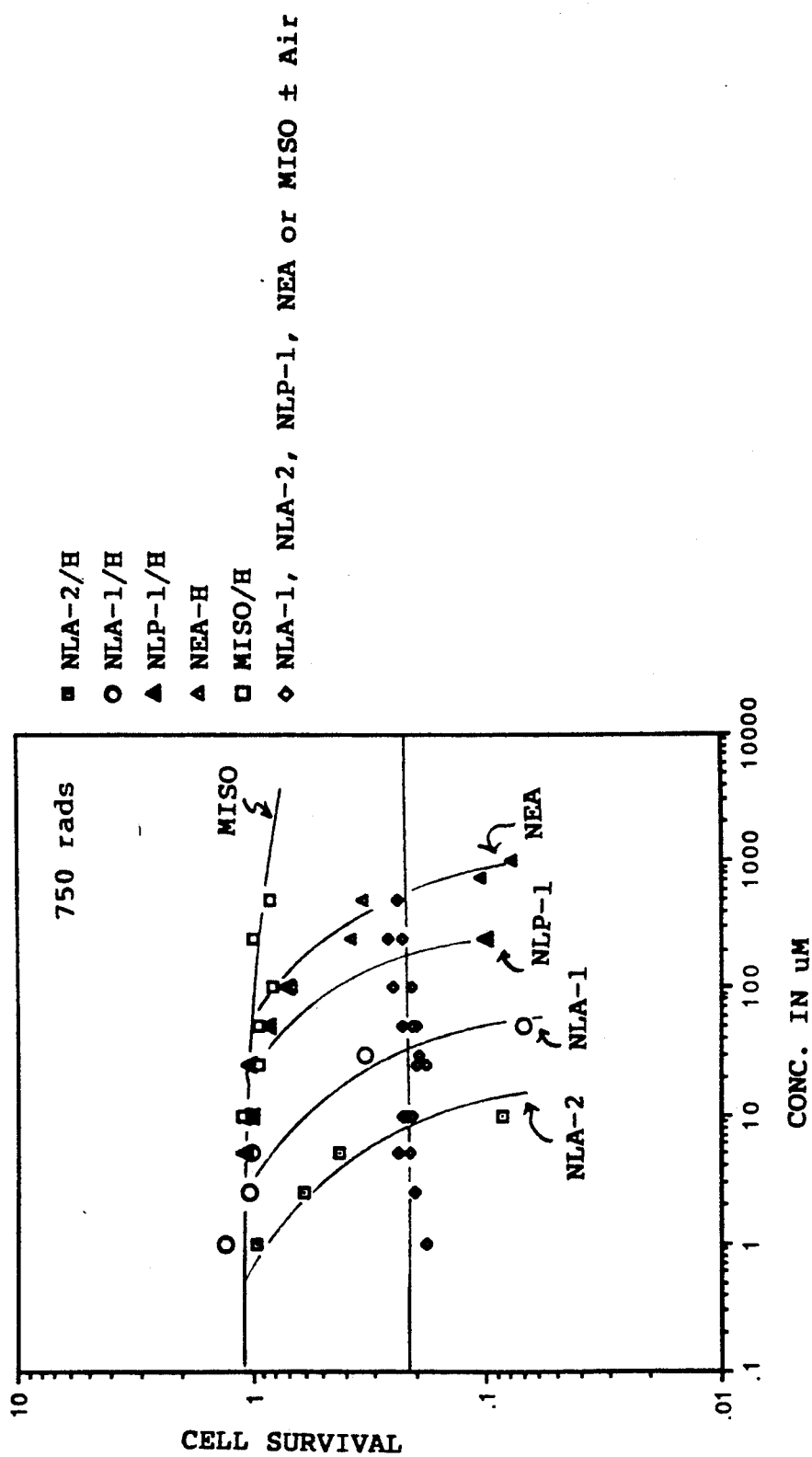
FIG. 4 is a graph showing radiation survival curves for the determination of isosensitization points at 750 rads (ISP) of NLA-1 under hypoxia (◯) and air ( ◇ ); NLA-2 under hypoxia ( ▫ ) and air ( ◇ ); NLP-1 under hypoxia ( ▲ ) and air ( ◇ ); NEA under hypoxia (Δ) and air ( ◇ ); and MISO under hypoxia (☐) and air ( ◇ ) for V-79 cells incubated with different concentrations of these compounds.

The various cell survivals were plotted against concentration in a logarithmic scale as shown in FIG. 4. The ISPs were obtained directly from the graph, as ordinates of the intersection points between the curves under hypoxia and aerobic conditions. All curves under aerobic conditions are identical and independent of drug concentration in the observed range.

As determined by the curves of FIG. 4, the ISP for NLA-1 is 15 $\mu$M and the ISP for NLA-2 is 7 $\mu$M. The corresponding ISPs for NLP-1 and NEA are 180 $\mu$M and 960 $\mu$M, respectively, while for MISO, the ISP is not reached at concentrations up to 2000 $\mu$M (data not shown for concentrations greater than 1000 $\mu$M). According to the ISP values, NLA-1 is 12 to 150 times better than NLP-1, NEA, and MISO as a radiosensitizer. NLA-2 is a 26 to 286 times better than the other compounds as a radiosensitizer.

In the following example the sensitizer enhancement ratio (SER) of NLA-1 and NLA-2 were obtained. SER is defined as the ratio of two radiation doses, with and without a sensitizer, required to reduce the surviving cell fraction to 1.0%.

EXAMPLE 6

Chinese hamster V-79 cells were grown, harvested and exposed to 25 $\mu$M NLA-1 or 10 $\mu$M NLA-2 for one hour and irradiated at 750 rads as described in Example 4. The cells were then plated for 4 days with results determined by a clonogenic assay as described in Example 3.

Figure 5:
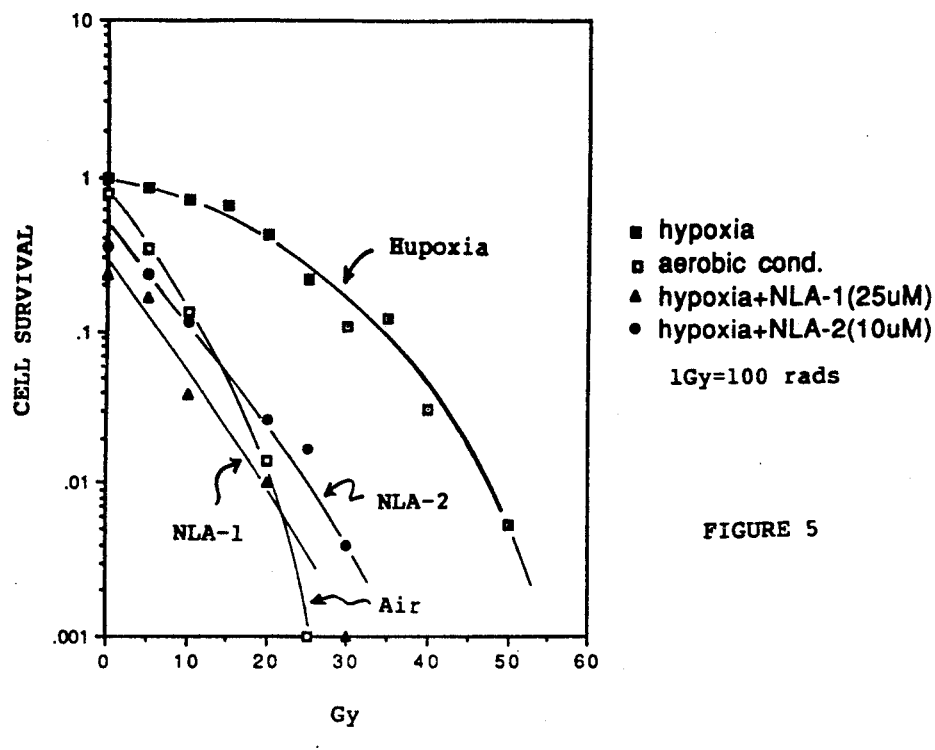
FIG. 5 is a graph showing radiation survival curves of V-79 cells first incubated with 25 μM NLA-1 under hypoxia ( ▲ ); 10 μM of NLA-2 under hypoxia ( ● ); and untreated cells under hypoxia ( ▫ ) and air (☐) at 0–50 gy (1 gy = 100 rads).

FIG. 5 shows the radiosensitization curves from which the SER determinations were made; every point on the graph represents the mean value of three independent experiments. The SER values are deleted for clarity. The SER for NLA-1 is 5.2 at 25 $\mu$M and 2.8 for NLA-2 at 10 $\mu$M. The oxygen enhancement ratio (OER) is 3.21. OER is the ratio of radiation dose under hypoxic conditions to the radiation dose under aerobic conditions which reduces the surviving fraction to 1.0%. Aerobic survival was the same whether NLA-1 or NLA-2 were present (not shown on graph).

As seen in FIG. 5, the greater radiosensitizing efficacy of NLA-1 as compared to that of NLA-2 may be due to the greater mobility of the 2-nitro imidazole ring around DNA due to the longer alkyl chain, with the consequences of a greater possibility of capturing radiation induced radicals. Attempts to optimize the SER of NLA-2 by using >10 $\mu$M concentrations were restricted due to the high hypoxic toxicity observed, even in the absence of radiation.

In the following example the chemosensitization effect of NLA-1 and NLA-2 on chemotherapeutic agent CCNU (1-(2-chloroethyl)-3-cyclohexyl-1-nitrosourea) is shown.

EXAMPLE 7

CCNU (Aldrich) was dissolved in absolute ethanol immediately prior to the experiment and added to Chinese hamster V-79 cells at different concentrations ranging from 0 mg/ml to 10 mg/ml in the presence or absence of 25 $\mu$M NLA-1 or 5 $\mu$M NLA-2 under hypoxic or aerobic conditions. The final concentration of EtOH was less than 1% in all cases.

Chinese hamster V-79 cells were incubated under hypoxia or air for 1 hour as described in the previous examples. NLA-1 or NLA-2 was added to give a final concentration of 25 $\mu$M or 5 $\mu$M respectively, followed immediately by the addition of CCNU to give a final concentration of 0 to 10 $\mu$g/ml. A clonogenic assay as described in Example 3 was used to calculate cell survival.

Figure 6:
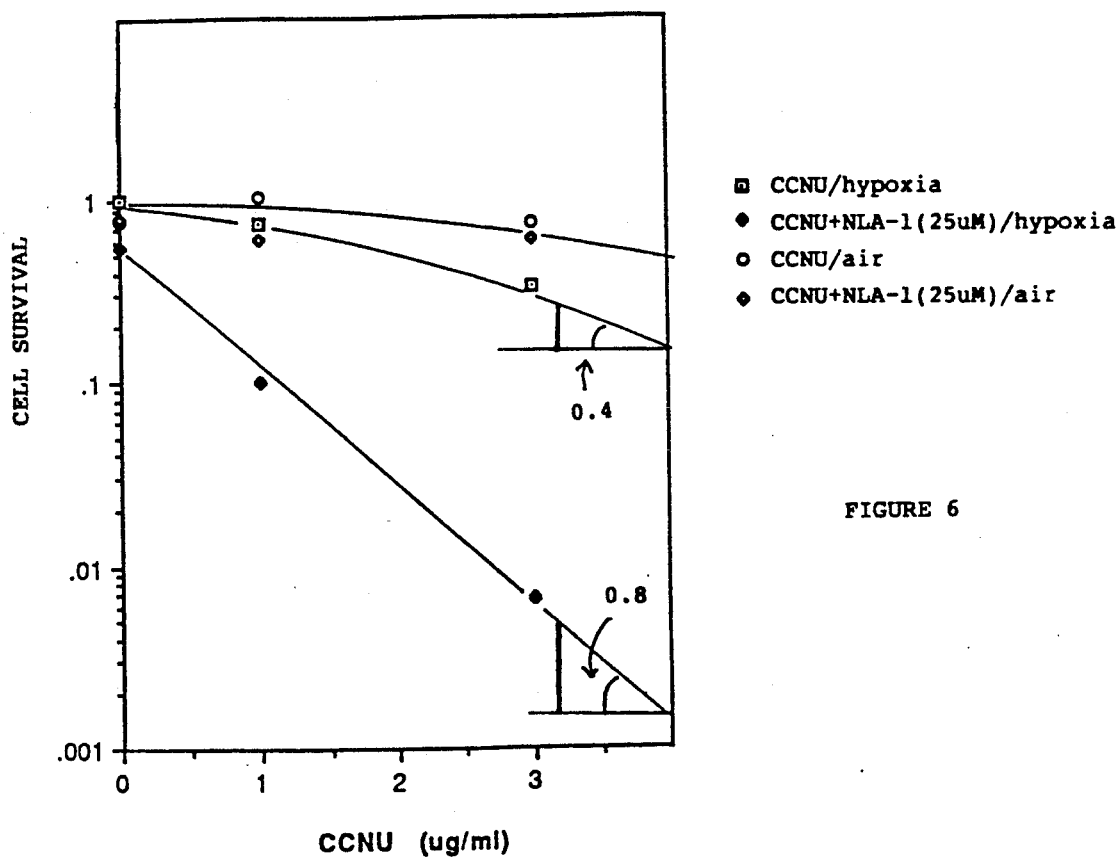
FIG. 6 is a graph showing chemosensitization of CCNU under hypoxia by 25 μM of NLA-1 ( ▫ ) = CCNU alone; ◆ = CCNU + NLA-1) and air (◯ = CCNU alone; ◇ = CCNU + NLA-1).
Figure 7B:
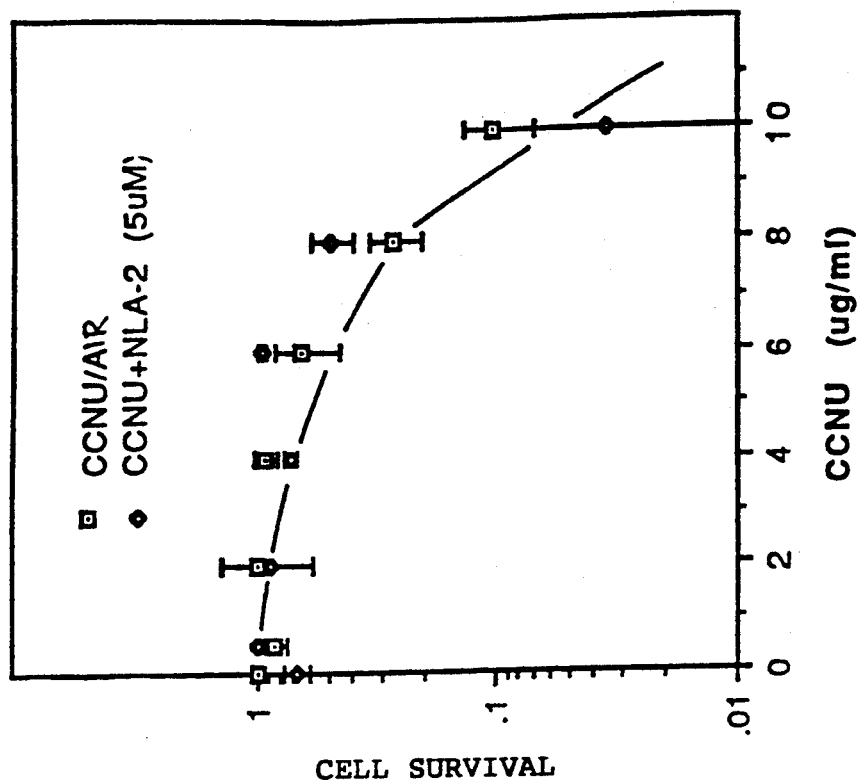
FIGS. 7a and 7b are graphs showing respectively chemosensitization of CCNU toxicity by 5 μM of NLA-2 under hypoxia ( ▫ = CCNU alone; ◆ = CCNU + NLA-2) and air ( ▫ = CCNU alone; ◇ = CCNU + NLA-2).
Figure 7A:
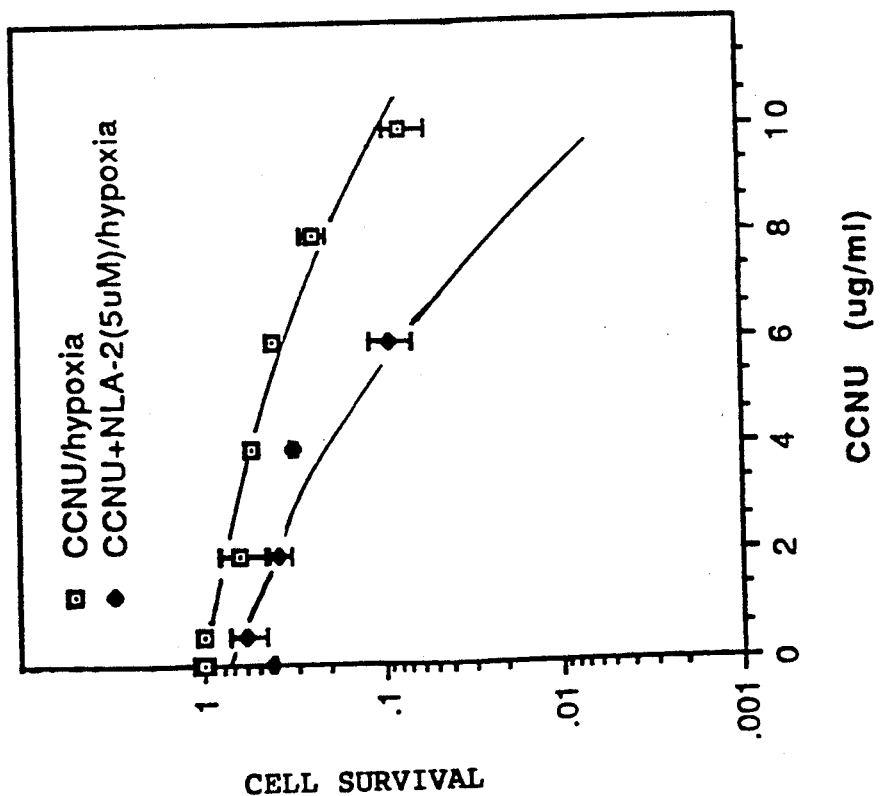

FIG. 5 shows the results of the studies using NLA-1. FIGS. 6a and 6b show the results of these studies with NLA-2 under hypoxic and aerobic conditions, respectively. As can be readily seen, both NLA-1 and NLA-2 demonstrate significant potentiation of CCNU's cytotoxicity in vitro under hypoxic conditions. No appreciable potentiation is seen to occur under aerobic conditions.

In the following example the LD$_{50}$, the dose required to kill 50% of the animals within seven days, was determined.

EXAMPLE 8

30 C3H (Harlan Sprague Dawley) mice in 5 groups of 6 mice were injected intraperitoneally with doses of 0–100 mg/kg of NLA-1 or NLA-2. Toxicity was assessed at 7 days. The $LD_{50}$ at 7 days for NLA-1 was 40 mg/kg and that for NLA-2 was 25 mg/kg respectively.

Although the invention has been described in detail for the purposes of illustration, it is to be understood that such detail is solely for that purpose and that variations can be made therein by those skilled in the art without departing from the spirit and scope of the invention, except as it may be limited by the claims.

What is claimed is:

1. A hypoxia selective cytotoxin of the formula

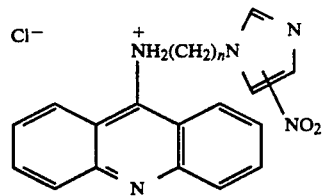

wherein n is from 1 to 5, and $NO_2$ is in the 2, 4 or 5-position of the imidazole.

2. The hypoxia selective cytotoxin of claim 1, wherein n is 2 or 3, and $NO_2$ is in the 2-position of the imidazole.

3. The hypoxia selective cytotoxin of claim 1 which is 9-[3-(2-nitro-1-imidazolyl) propylamino] acridine hydrochloride (NLA-1).

4. The compound of claim 1 which is 9-[2-(2-nitro-1-imidazolyl) ethylamino] acridine hydrochloride (NLA-2).

* * * * *